US008688418B2

(12) United States Patent
Sukup et al.

(10) Patent No.: US 8,688,418 B2
(45) Date of Patent: Apr. 1, 2014

(54) ENGINEERED METHODOLOGY FOR DESIGN VERIFICATION AND VALIDATION OF ULTRA-DEEP HIGH PRESSURE HIGH TEMPERATURE OIL AND GAS WELL CONTROL EQUIPMENT

(75) Inventors: Richard Anthony Sukup, Hico, TX (US); J. Robert Sims, Basking Ridge, NJ (US); Ravi M. Krishnamurthy, Houston, TX (US); David B. Lewis, Carrollton, TX (US)

(73) Assignee: McMoRan Oil & Gas, LLC, New Orleans, LA (US)

( * ) Notice: Subject to any disclaimer, the term of this patent is extended or adjusted under 35 U.S.C. 154(b) by 272 days.

(21) Appl. No.: 13/223,485

(22) Filed: Sep. 1, 2011

(65) Prior Publication Data

US 2013/0060536 A1    Mar. 7, 2013

(51) Int. Cl.
*G06F 7/60*     (2006.01)
*G06F 17/10*    (2006.01)
*G06F 17/50*    (2006.01)

(52) U.S. Cl.
CPC .................... *G06F 17/5018* (2013.01)
USPC .................................................. 703/2; 703/7

(58) Field of Classification Search
USPC ........................................... 703/2, 7; 700/275
See application file for complete search history.

(56) References Cited

U.S. PATENT DOCUMENTS

| | | | |
|---|---|---|---|
| 6,431,291 B1 | 8/2002 | Moore et al. | |
| 7,204,152 B2 | 4/2007 | Woodward et al. | |
| 2008/0015827 A1* | 1/2008 | Tryon et al. | 703/2 |
| 2008/0195357 A1 | 8/2008 | Gustafson et al. | |
| 2008/0319720 A1 | 12/2008 | Ellis et al. | |
| 2009/0091053 A1 | 4/2009 | Polizzotti et al. | |
| 2010/0042379 A1 | 2/2010 | Minnaar et al. | |
| 2010/0292966 A1 | 11/2010 | Wang et al. | |

FOREIGN PATENT DOCUMENTS

WO    WO2009116048 A2    9/2009

OTHER PUBLICATIONS

Brownlee, J. K., et al. "97590-Selection and Qualification of Materials for HPHT Wells." SPE High Pressure/High Temperature Sour Well Design Applied Technology Workshop, The Woodlands, Texas, May 17-19, 2005.
Young, Kenneth, et al. "97595-Updated Design Methods for HPHT Equipment." SPE High Pressure/High Temperature Sour Well Design Applied Technology Workshop, The Woodlands, Texas, May 17-19, 2005.

(Continued)

*Primary Examiner* — Eunhee Kim
(74) *Attorney, Agent, or Firm* — Jones Walker LLP (57) ABSTRACT

A process for the verification and validation testing of equipment and components for drilling, completion, production and general well construction (typically such as subsurface safety valves, wellhead trees, blowout preventers and wireline pressure control equipment) to determine the suitability of such equipment for use in oil and gas wells in high pressure high temperature environments. In particular, the process of the present invention comprises, among other steps, the steps of analyzing such components using an elastic-plastic finite element model with respect to certain preset load conditions and establishing stable model convergence, conducting a ratcheting assessment by running analysis on such model on all components that exhibit local plasticity, and examining all components to determine fatigue sensitive locations and subjecting such components to a fatigue analysis. The process may further comprise a process for qualifying the materials to be used in the manufacture of the equipment components with respect to their ability to withstand high pressure and high temperature environmental conditions.

43 Claims, 4 Drawing Sheets

(56) References Cited

OTHER PUBLICATIONS

Marsh, Jonathan, et al. "130716-Materials Selection for HP/HT Developments" SPE International Conference on Oilfield Corrosion, Aberdeen, United Kingdom, May 24-25, 2010.
Koeck, F., D. MacFarlane, and H. B. Skeels. "18076-Future Consideration for HPHT Equipment and Systems." 2006 Offshore Technology Conference, Houston, Texas, May 1-4, 2006.
PCT/US2012/051666, Notification of Transmittal of the International Search Report and the Written Opinion of the International Searching Authority, or the Declaration; International Search Report; Written Opinion of the International Searching Authority, issued by the USPTO as the International Searching Authority on Dec. 12, 2012.
Huang, J. Y., and T. M. Miller. "The application of finite element analysis to VIP compressor cylinder design." International Compressor Engineering Conference, Paper 1041, Purdue University e-Pubs, 1994.
Rahman, Syed Mizanur, "Finite element analysis and related numerical schemes for ratcheting simulation." A dissertation presented to North Carolina University, 2006.
API Technical Report PER15k, DRAFT, Protocol for Verification and Validation of HPHT Equipment, American Petroleum Institute, 2010, pp. 1-126.
ANSI/API Specification 6A, Specification for Wellhead and Christmas Tree Equipment, 20th Edition, American Petroleum Institute, Oct. 2010, pp. 1-448.
ASME, Section VIII, Division 3: Alternative Rules for Construction of High Pressure Vessels. Rules for Construction of High Pressure Vessels. ASME Boiler and Pressure Vessel Code. The American Society of Mechanical Engineers. 2010, pp. 1-382.
2011a Addenda, ASME, Section VIII, Division 3: Alternative Rules for Construction of High Pressure Vessels. Rules for Construction of High Pressure Vessels. ASME Boiler and Pressure Vessel Code. The American Society of Mechanical Engineers, with Interpretations vol. 61, pp. 1-392.
ANSI/NACE International MR0175/IS0 15156. Petroleum and natural gas industries—Materials for use in H2S—containing environments in oil and gas production. American National Standard, Second Edition, 2009. Part 1: General Principles for Selection of Cracking-Resistant Materials; Part 2: Cracking-resistant carbon and low alloy steels, and the use of cast irons; Part 3: Cracking-resistant CRAs (corrosion-resistant alloys) and other alloys; Technical Circular 1 to Part 3:2-11; Technical Circular 1 to Part 2:2011, pp. 1-166.
API, 579-1/ASME FFS-1 (API 579 Second Edition) "Fitness-for-Service." Am Soc Mech Eng. 2007, Parts 1-9, pp. 1-335.
API, 579-1/ASME FFS-1 (API 579 Second Edition) "Fitness-for-Service." Am Soc Mech Eng. 2007 Parts 10-13, pp. 1-190.
API, 579-1/ASME FFS-1 (API 579 Second Edition) "Fitness-for-Service." Am Soc Mech Eng. 2007, Annex A-B4, pp. 1-167.
API, 579-1/ASME FFS-1 (API 579 Second Edition) "Fitness-for-Service." Am Soc Mech Eng. 2007, Annex C-D, pp. 1-231.
API, 579-1/ASME FFS-1 (API 579 Second Edition) "Fitness-for-Service." Am Soc Mech Eng. 2007, Annex E-K, pp. 1-197.
API, 579-1/ASME FFS-1 (API 579 Second Edition) "Fitness-for-Service" Am Soc Mech Eng. 2007, Errata, Feb. 2009, pp. 1-168.

\* cited by examiner

FIG. 4

ENGINEERED METHODOLOGY FOR DESIGN VERIFICATION AND VALIDATION OF ULTRA-DEEP HIGH PRESSURE HIGH TEMPERATURE OIL AND GAS WELL CONTROL EQUIPMENT

BACKGROUND OF THE INVENTION

1. Field of the Invention

This invention relates to a process for verification and validation of the design of oil and gas equipment in order to determine whether such equipment is capable of withstanding certain high pressure and high temperature environments (generally referred to in the oil and gas industry as the "ultra-deep high pressure high temperature" environment ("HPHT")) that are anticipated to be experienced in the exploration, drilling, completion and production of HPHT oil and gas wells. Typically, all components of the equipment that will be subject to such HPHT environments and that either contain fluid pressure or that are important to ensure the serviceability and fitness of such equipment for such environments should be analyzed prior to the implementation of the well to ensure the success of the well. The types of oil and gas equipment typically used in such exploration, drilling, completion and production operations and that may serve as the types of equipment that are suitable for such analysis include subsurface safety valves ("SCSSV"), wellhead trees, blowout preventers ("BOP") and wireline pressure control ("WPC") equipment, but may also include other types of well control equipment.

2. Description of the Related Art

The design of oil and gas equipment for the oil and gas industry typically has involved following a process similar to the following: (i) identify the need or problem, (ii) research the need or problem, (iii) design and develop possible solutions, (iv) construct a prototype, (v) test and evaluate the solutions, and (vi) overhaul the solutions based on information gathered during the tests and presentation. In the HPHT environment, steps (iii) and (v) have been proven to be very important because of the unique environmental challenges presented by the HPHT environment. The design verification and validation process of the present invention is useful in the art because it assists designers and users of oil and gas equipment for the HPHT environment in relation to steps (iii) and (v).

It is also recognized that design verification and validation processes are well known outside of the oil and gas industry and are used to analyze pressure vessel designs for various industries. Such pressure vessel design processes are further described in ASME Section VIII, Division 3, 2010 Edition (including the 2011 Addenda). Although many of the steps described in the process of the present invention are disclosed in ASME Section VIII, Division 3, 2010 Edition (including the 2011 Addenda), the present invention, in the preferred embodiment, uses such processes to validate and verify the design of oil and gas equipment for the HPHT environment in a manner not presently practiced in the oil and gas industry. The steps of the design verification and validation process described below relate to the application of the process to certain types of oil and gas equipment used in the HPHT environment. The types of equipment suitable for analysis through such process, in the preferred embodiment, are SCSSV's, wellhead trees, BOP's, WPC and other well control equipment.

SUMMARY OF THE INVENTION

The design verification and validation process described below analyzes oil and gas equipment components for use in the HPHT environment. The objective of the process is to ensure that such oil and gas equipment components will withstand HPHT environments and not malfunction or fail for the serviceable life of the well. The conditions of the HPHT environment subject the equipment component to stress and load conditions that are extreme. As an example, such environmental conditions are assumed to be greater than 20,000 psi for pressure and/or greater than 400° F. for bottom hole static temperature.

The further objectives of the design verification and validation process of the present invention are, depending on the circumstances, to confirm the mechanical properties of the components at ambient to high temperature, to determine the components' resistance to corrosion, to determine the components' resistance to cracking, and to further determine the extent of potential cracking or other enhanced material failure due to cumulative plasticity at high temperatures and due to the conditions of the HPHT downhole environment.

These and other objects and features of the present invention will become apparent from the following Detailed Description and the following drawings.

BRIEF DESCRIPTION OF THE DRAWINGS

For a further understanding of the features and advantages of the present invention, reference should be made to the following Detailed Description taken in conjunction with the accompanying drawings and wherein.

DETAILED DESCRIPTION OF THE PREFERRED EMBODIMENT

Figure 1:
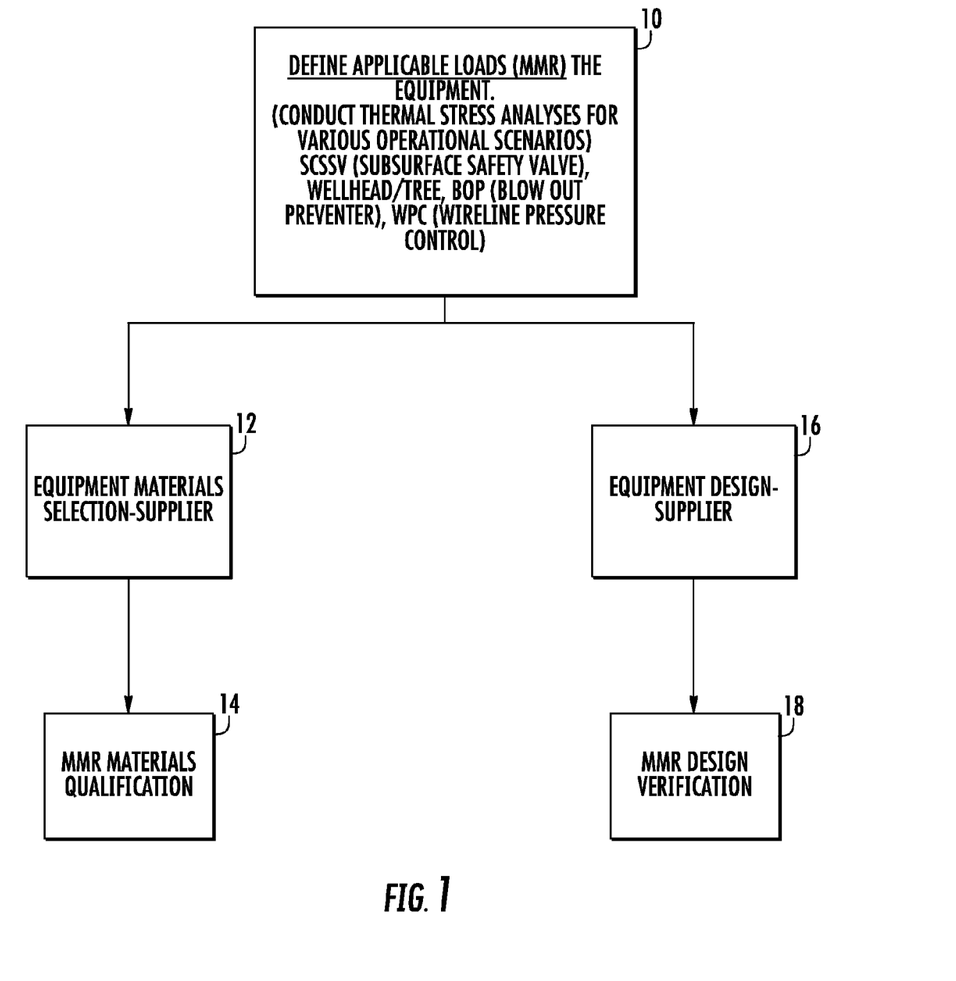
FIG. 1 is a block diagram that shows certain preliminary considerations that relate to materials qualification and equipment design processes in connection with oil and gas equipment components.

Reference is made to FIG. 1 showing certain preliminary considerations that relate to the use of the process described below in the construction and implementation of oil and gas equipment in the HPHT environment. As shown in step 10, the oil and gas equipment on which the design verification and validation process is used, in its preferred embodiment, are SCSSV's, wellhead trees, BOP's, WPC's and other well control equipment. As shown in step 12, the owner or operator of an HPHT well may desire to determine whether a supplier is providing materials to be used in the design and manufacture of oil and gas equipment that are suitable for the HPHT environment and to require that such supplier make proper selections of such materials. A supplier of such oil and gas equipment may also independently desire to use materials qualification processes for such purposes. In step 14, in some cases, materials may be selected by the owner or operator of the well for use in connection with the manufacture of the equipment, and, therefore, the owner or operator may desire to use materials qualification processes in order to avoid equipment components manufactured using unsuitable materials. In step 16, assuming proper materials have been selected, a supplier may also desire to subject the design of such oil and gas equipment to the design verification and validation process to ensure the suitability of such equipment for the HPHT environment. The owner or operator of the well may also desire to use the design verification and validation process to further confirm the suitability of such equipment for use in the HPHT environment as indicated in step 18.

Materials Qualification.

Figure 2:
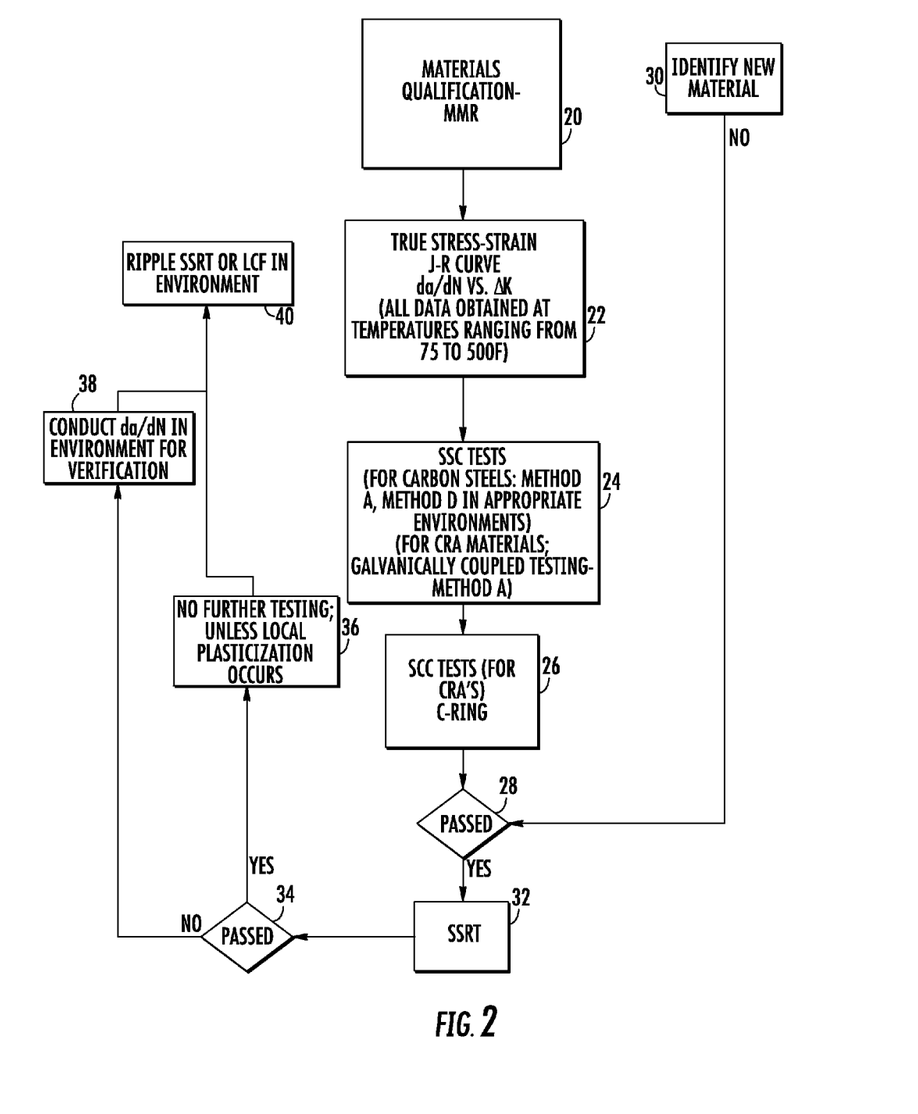
FIG. 2 is a block diagram that shows the steps comprising the materials qualification process used in connection with the design verification and validation process of the present invention for use in the manufacture of oil and gas equipment components.

FIG. 2 describes in greater detail the materials qualification process, referred to generally as step 20, that may be used in association with the design verification and validation process. The design verification and validation process may utilize data developed in the materials qualification process with respect to the materials selected for the equipment. The materials qualification testing used in such process is intended to develop such data for use as inputs in the design verification and validation process to ensure the suitability of the materials for the HPHT application. Such data may include: (i) the mechanical properties (stress-strain J-R curve (J-integral-crack extension)) of the equipment at ambient to high temperature, (ii) the resistance of the material to corrosion (pitting, general or flow induced), (iii) the resistance of the material to cracking (SSC (sulfide stress cracking), SCC (stress corrosion cracking), fatigue, at higher temperatures), and (iv) the resistance of the material to cracking or other enhanced material failure due to cumulative plasticity at high temperatures (which will depend on the application if the equipment is exposed to plastic loading).

As shown in step 22, the data relating to the material mechanical properties of the selected materials is obtained in the materials qualification process for application to the design verification and validation process. Such material mechanical properties data are developed using computer modeling and other physical testing techniques. The material mechanical properties data developed from such testing include the engineering or the true stress-strain curve and the J-R curve as such are generally known in the industry. Such material mechanical properties data are obtained for temperatures that may range from 75° F. to 500° F. depending on the application.

As an additional challenge, the HPHT production environment may include the production of acid gases (carbon dioxide and hydrogen sulfide) with water. This factor is also considered as part of the materials qualification process in order to demonstrate that there is no reduction in the mechanical properties of the materials as a result of such conditions.

As shown in FIG. 2, upon completion of the true stress-strain curve and the J-R curve (otherwise referred to in the art as the J-integral-crack extension curve) of step 22, the selected materials are subjected to SSC (otherwise referred to in the art as sulfide stress cracking) tests as shown in step 24. With respect to carbon steels, such tests may include the Method A (NACE MR0175) and/or Method D (NACE MR0175) in appropriate environments as known to one of ordinary skill in the art. Similarly, for CRA (otherwise referred to in the art as corrosion resistant alloys) materials, such materials are subjected to galvanically coupled testing—Method A (NACE MR0175). Following such testing in step 24, such materials are further subject to SCC tests as shown in step 26. CRA materials are further evaluated for corrosion resistance using autoclave tests at various temperatures as known in the art. To validate the components with respect to cracking resistance, the components should further be evaluated using a C-ring test, a DCB test or a Method A type (NACE MR0175) tensile test applying protocols applicable to the HPHT environment as further referenced in step 26. In such tests, the materials must demonstrate resistance to corrosion and cracking. If such materials fail such tests, the materials are not suitable for use in the HPHT environment. Following the successful completion of these tests, the additional steps set forth below are undertaken as further part of the materials qualification process.

The cracking resistance of the materials is determined in either step 24 or step 26 using the appropriate SCC and/or SSC tests. In such cracking tests, the stress and strain applied to the material sample should reflect the anticipated loading on the equipment components. The test environments should further be established to reflect the anticipated HPHT downhole environments. The testing periods will vary from 30 to 90 days depending on the test and material type.

In step 28, if the materials do not pass such tests, such materials are deemed not suitable for use in the HPHT environment and a new material must be identified for use in such component as shown in step 30 The materials qualification process should then be repeated for any new materials selected. If the materials are determined to satisfy such tests, then additional modeling testing is performed with respect to such materials as further described below.

As shown in step 32 of FIG. 2, an additional test to be performed in the materials qualification process includes the application of an SSRT test (otherwise referred to in the art as the slow strain rate testing). The SSRT is applied in accordance with practices known by those of ordinary skill in the art. In step 34, it is determined whether or not such materials have passed the SSRT test. However, for certain components where there is cumulative local plasticization as shown in step 36, additional testing may be warranted. If the material demonstrates either secondary cracking or ratio's that are less than 0.9 then additional fatigue testing or ripple SSRT or LCF (otherwise known as low cycle fatigue) in HPHT downhole environment will be necessary as shown in step 38 and step 40.

Such testing concludes the materials qualification process. The materials qualification process ensures that a material used in an equipment component has a strength reflective of the design assumptions for the HPHT environment.

Design Validation and Verification.

Figure 3:
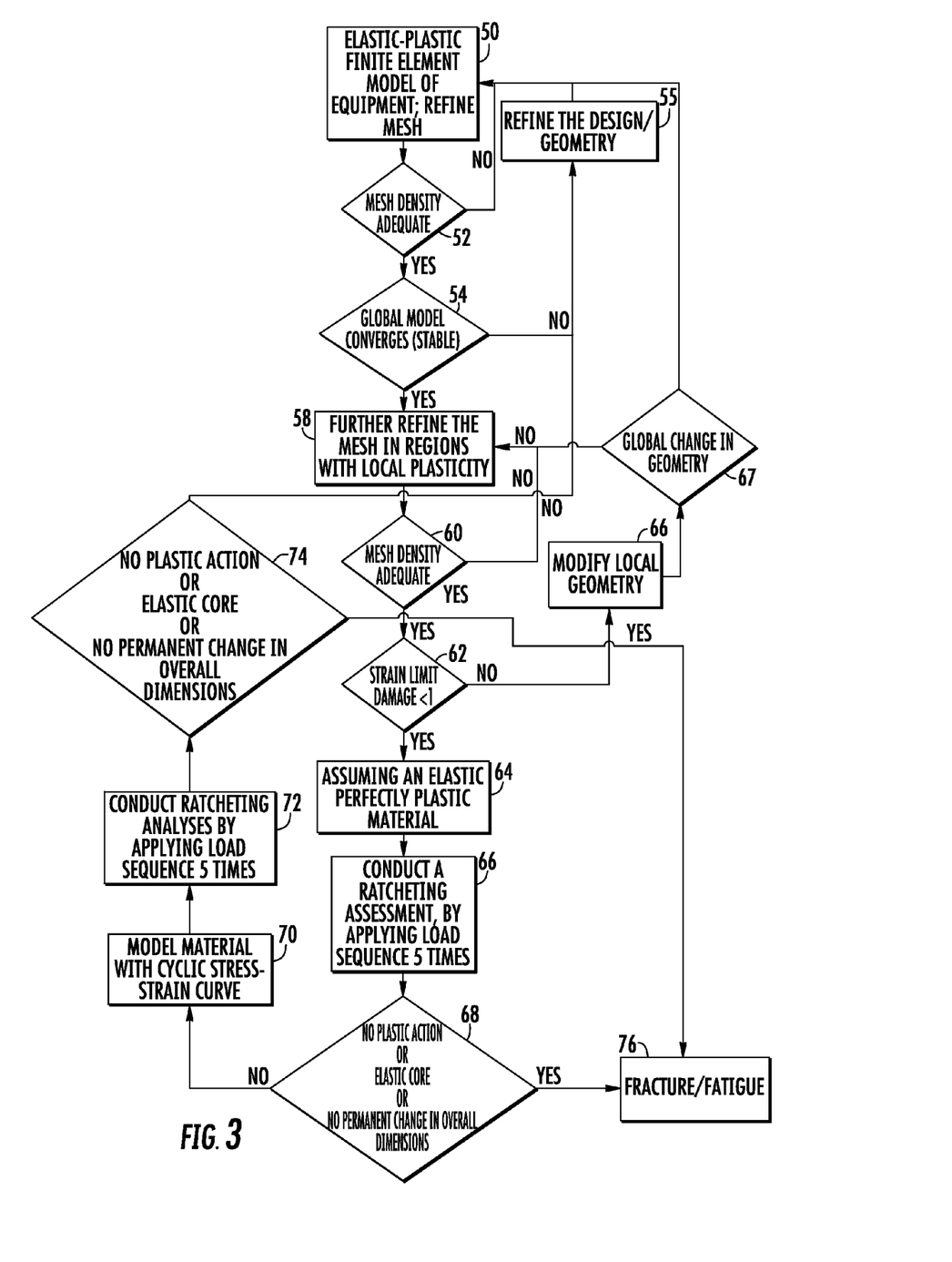
FIG. 3 is a block diagram that shows the steps comprising the elastic-plastic finite element modeling and the ratcheting assessment of the design verification and validation process of the present invention for oil and gas equipment components.
Figure 4:
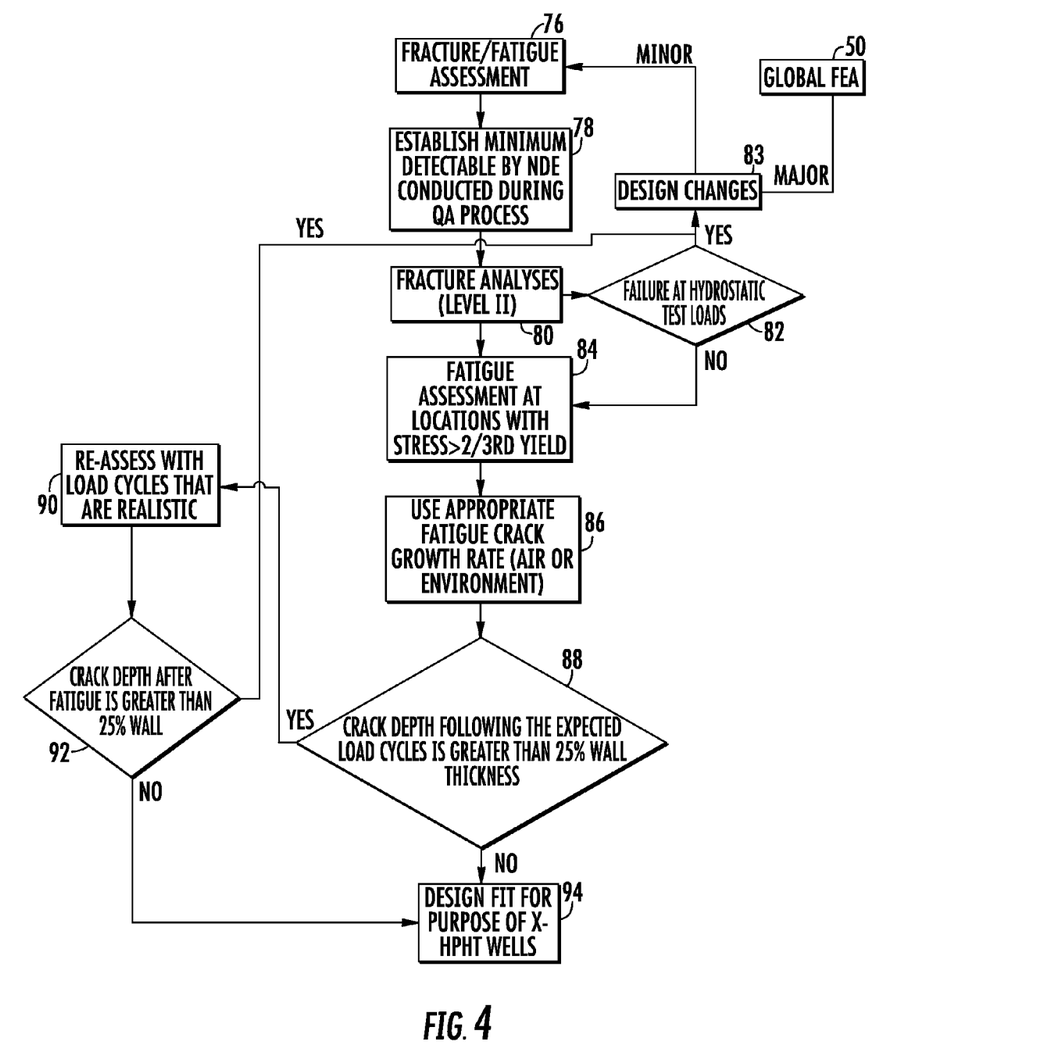
FIG. 4 is a block diagram that shows the steps comprising the fatigue assessment for the design verification and validation process of the present invention for oil and gas equipment components.

The design validation and verification process of the present invention is further shown in FIG. 3 and FIG. 4. The design validation and verification process of the present invention, in the preferred embodiment, is applied to SCSSV's, wellhead trees, BOP's, WPC's and other well control equipment for the HPHT environment. Such equipment is verified and validated pursuant to the design validation and verification process for operation as either load bearing or pressure containing equipment, and for possible exposure to well produced fluids, well kill fluids or drilling completion fluids in the actual well environment.

In preferred embodiment, the design validation and verification process comprises, in addition to the other steps described below, primarily three steps: (i) the performance of an elastic-plastic finite element computer model, (ii) a ratcheting assessment analysis and (iii) a fatigue analysis. Such analysis will be performed using computer modeling applications as known in the art. In many embodiments, such analysis will also be performed in reference to certain preset load combinations on a global basis to the equipment component as well as on a localized basis on particular surfaces and contours of the equipment component using surface areas defined using a mesh definition. The mesh definition may be further refined as part of the process as further described below.

In developing the preset load conditions for such analysis, all load combinations (e.g. static, transient, or cyclic) that the equipment may be subject to in the HPHT environment are considered. The preset load conditions are thus a set of predefined loads to be used for the design verification and validation of all equipment components subjected to the design verification and validation process in order to model the HPHT environment. Possible loads are considered and defined for purposes of the modeling and include loads relating to planned and unplanned activities during the life of the well, post-manufacturing loads and routine testing loads. Such testing loads may include manufacturing testing and monthly SSV (subsurface valve) testing. The unplanned activities include well reservoir management, surface repair, subsurface repair, production or equipment problems that result in cessation of production, weather induced events, stimulation activities and periodic testing scenarios. The total number of cycles and load amplitudes are defined using all the anticipated activities on the wellbore that will cause changes in temperature and pressure. Following such load definitions, the tables (KD 230.4 and KD-230.2) from ASME Section VIII, Division 3 are utilized to establish the multipliers, and such tables are hereby incorporated by reference into this application.

The load case combinations and load factors used to develop the preset load conditions are further described in Table 1 set forth below.

TABLE 1

Load Case Combinations and Load Factors for an Elastic-Plastic Analysis
Design Conditions - See Nomenclature in Table 2

| Criteria | Required Factored Load Combinations |
| --- | --- |
| Global Criteria | 1) $1.8(P + P_s + D)$ |
| | 2) $1.58(P + P_s + D + T) + 2.03L$ |
| | 3) $1.58(P + P_s + D) + \max [1.28L, 0.65W]$ |
| | 4) $1.58(P + P_s + D) + 1.28W + 1.28L$ |
| | 5) $1.58(P + P_s + D) + 1.28E + 1.28L$ |
| Local Criteria | $1.28(P + P_s + D)$ |
| Serviceability Criteria | Per Specification |

Further, in developing such preset load conditions, the load descriptions further described in Table 2 are considered as those loads that are anticipated to be applicable to the HPHT environment and primarily relate to temperature, pressure and weight loading conditions. As further described below, such load combinations are intended to simulate various circumstances that may occur in the HPHT environment.

TABLE 2

Load Descriptions

| Design Load Parameter | Description |
| --- | --- |
| P | Internal and external design pressure |
| $P_s$ | Static head from liquid or bulk materials |
| D | Dead weight of the component, contents, and appurtenances at the location of interest, including the following: Weight of component including internals, supports (e.g. skirts, lugs, saddles, and legs), and appurtenances (e.g. platforms, ladders, etc.) Refractory linings, insulation Static reactions from the weight of attached equipment, such as motors, machinery, other components, and piping |

TABLE 2-continued

Load Descriptions

| Design Load Parameter | Description |
| --- | --- |
| L | Appurtenance Live loading Effects of fluid momentum, steady state and transient |
| E | Loads due to "worst case" wave action (platform motion, etc.) |
| W | Wind Loads |
| T | Is the self-restraining loan case (i.e. thermal loads, applied displacements). This load case does not typically affect the collapse load, but shall be considered in cases where elastic follow-up causes stresses that do not relax sufficiently to redistribute the load without excessive deformation. |

Once the preset load conditions are predefined, the design verification and validation process involves the steps shown in FIG. 3. As shown in step 50 of FIG. 3, the equipment components are analyzed for static strength using an elastic-plastic finite element model. The elastic-plastic finite element model is often referred to as the "FEA". The elastic-plastic finite element model analyzes the equipment components for global static strength and for local plasticity in accordance with the preset load conditions.

The elastic-plastic finite element model is constructed based on the method generally described and known by one skilled in the art in ASME Section VIII, Division 3, 2010 Edition (through the 2011 Addenda), paragraph KD-231, and which is hereby incorporated by reference into this application. Also, in the running of the model to determine any issues relating to the plasticity of the inside corners, notches or any other source of stress concentration in the equipment component, the elastic-plastic finite element model is based on the methods described in ASME Section VIII, Division 3, 2010 Edition (through the 2011 Addenda), paragraph KD-232, and such description is hereby incorporated by reference into this application. Also, nonlinear geometry shall be used in such modeling and all components shall be modeled based on their configuration including any anticipated cladding, weld overlay and integral liners. In assuming the least favorable combination of dimensional tolerances for each component, such combination is selected from the range specified in the design, for example, for a cylindrical part, the maximum outside diameter and the minimum wall thickness shall be used.

The step of setting the initial mesh density of the component for the purposes of the process is also included in step 50. In step 52, it is determined whether or not the initial mesh density is adequate for purposes of continuing the analysis. If the initial mesh density is not adequate, a new mesh refinement is selected and step 50 is re-performed. If the initial mesh density is adequate, the elastic-plastic finite element model is run as shown in step 54 to determine whether the model results in a stable model convergence based on all of the preset load conditions with the appropriate load factors. If the model is not stable, the design or geometry of the equipment component must be refined as shown in step 55 and steps 50 and 52 are repeated with respect to the new design and geometry.

If the model is stable for all preset load conditions, then step 58 is performed. As shown in step 58, the mesh density in portions of the equipment component that demonstrate local plasticity is further studied and refined. Although other refinement parameters may be selected, in the preferred embodiment, the mesh refinement process includes refinement of the initial mesh density by a factor of 2. The mesh refinement process also requires a change in the plastic strain experienced by the portion of the equipment component from the refined mesh to be less than a certain pre-selected mesh refinement percentage change. Depending on the circumstances, and in various embodiments, the pre-selected mesh refinement percentage change in the plastic strain that will be acceptable will range from less than 5% to less than 2%. The pre-selected mesh refinement percentage change is selected from the less than 5% to less than 2% range based on whether the acceptance criteria relates to global or local strength evaluation with respect to the equipment component being analyzed. In step 60, it is determined whether the mesh density is adequate as a result of such mesh refinement process. If the mesh density is not adequate, the mesh density is further refined by repeating step 58. If the mesh density is determined to be adequate, then step 62 is performed.

In step 62, an elastic-plastic finite element model analysis of all the highly stressed locations of the equipment component identified by the model is performed to determine the strain limit damage. The curves used as input to such analysis may be generated using the method known by one skilled in the art and described in ASME Section VIII, Division 3, 2010 Edition (through the 2011 Addenda), paragraph KD-231.4, and the description of such method is hereby incorporated by reference into this application. In all cases, the curves shall be adjusted to the minimum specified yield strength. If the strain limit damage resulting from such analysis for the location is less than an acceptable set strain limit damage amount, then the process is continued and step 64 is performed. For purposes of the preferred embodiment of the process of the present invention, the set strain limit damage amount is set at 1, but other amounts may be selected for the acceptable stain limit damage amount in other embodiments. If the strain limit damage is not less than 1, the acceptance criteria are not satisfied and the local geometry for the equipment component is further modified as shown in step 65.

At step 67, it is further determined whether modifications to the geometry for the equipment component must be performed to achieve strain limit damage that is less than the set strain limit damage amount. If only a modification to the local geometry for the equipment component is required, steps 58 and 62 are repeated. If the global geometry for the equipment component must be modified as determined in step 67, then step 50 is re-performed and the process steps of 50 through 62 must be re-performed with respect to the modified global geometry to ensure suitability of the equipment component.

In step 64, the equipment component is modeled using an elastic-perfectly plastic material. A ratcheting assessment is performed as a step in the process of the present invention as indicated in step 66. The ratcheting assessment is applied to all equipment components that exhibit local plasticity at the maximum (worst case) combination of preset load conditions. The purpose of such ratcheting assessment is to determine the resistance of the equipment component to such ratcheting. The ratcheting assessment is performed in accordance with the method in ASME Section VIII, Division 3, 2010 Edition (through the 2011 Addenda) paragraph KD-234, and the description of such method is hereby incorporated by reference into this application. In the ratcheting assessment, the preset load conditions sequence is applied to the equipment component in the model at least 5 times in the preferred embodiment. It is recognized that such load conditions could be applied in lesser or greater amounts of cycles in other embodiments. The present invention varies from the provisions of ASME Section VIII, Division 3, 2010 Edition (through the 2011 Addenda) which only specifies that such ratcheting assessment shall involve the application of such preset load conditions for a minimum of 3 cycles.

In step 68, it is determined whether the ratcheting criteria have been satisfied as a result of the ratcheting assessment. These criteria are set forth in ASME Section VIII, Division 3, 2010 Edition (through the 2011 Addenda), paragraph KD-234, and such criteria are hereby incorporated by reference into this application. For an equipment component to satisfactorily complete the ratcheting assessment, the model must evidence that the component has satisfied at least one of the following ratcheting criteria: (i) a condition of no plastic action in the component, or (ii) a condition where an elastic core exists at the primary load bearing boundary of the component, or (iii) a condition in which there is no permanent change in the dimensions of the component. It is necessary only that one of these criteria described in (i), (ii) or (iii) be satisfied to complete the ratcheting assessment. A further discussion of each of these criteria is described below.

The first ratcheting criterion involves determining whether or not there is no plastic action (i.e. zero plastic strains incurred) in the component. If this situation exists for the first application of a load, the ratcheting assessment is not needed, since the component would not have exhibited local plasticity at the maximum (worst case) combination of the preset load conditions, which would have exempted it from the ratcheting assessment of step 66. However, it is common for components to exhibit plasticity on the first application of the loads, but to "shake down" after one application of the load, such that subsequent loads do not result in additional plastic strain. This situation can be illustrated by the autofrettage process in a thick wall cylinder, in which yielding at the bore surface of the cylinder occurs at the autofrettage pressure. When the pressure is reduced to ambient, the bore is placed in compression by the elastic contraction of the outer portion of the cylinder. If the bore does not "reverse yield" in compression when the pressure is removed, subsequent pressure cycles to a pressure at or below the autofrettage pressure will result in a monotonic, linear increase in the stress at the bore with no additional plastic action.

The second ratcheting criterion involves determining whether or not there is an elastic core in the primary load bearing boundary of the component. To continue with the above example, if the cylindrical component had a very thick wall, and was subjected to a very high autofrettage pressure, the bore might yield in compression when the pressure is reduced to ambient. In that case, the bore will yield again in tension when the component is pressurized back to the autofrettage pressure. This cyclic plasticity will continue with each subsequent pressure cycle. Although this is a concern for the design fatigue life, it is not a ratcheting condition because the outer portion of the cylinder remains elastic at all times. The elastic portion prevents progressive plastic deformation (ratcheting) of the material at the bore.

The third ratcheting criterion involves determining that there is not a permanent change in the overall dimensions of the component. This can be demonstrated by developing a plot of relevant component dimensions versus time between the last and the next to the last cycle. The term "overall dimensions" should be interpreted to mean any dimensions such as diameter, overall length, flatness of flat heads and other flat components. Note that FEA programs will give small changes in dimensions from one cycle to the next when plasticity is involved because of differences in load increment and numerical resolution in the solver. This should be considered when deciding whether there is a permanent change in the overall dimensions. As a minimum, dimensional changes during the 5 cycles of the application of the preset load conditions shall not be greater than the dimensional tolerances on the manufacturing drawings.

If the ratcheting criteria are achieved, the fatigue analysis shown as step 76 and further described in FIG. 4 is performed.

As shown in step 70, if at least one of the ratcheting criteria are not met, the analysis may be repeated using the cyclic true stress—strain curves for the materials used in construction. These curves may be generated using the method in ASME Section VIII, Division 3, 2010 Edition (through the 2011 Addenda), paragraph KD-360, and such method is hereby incorporated by reference into this application. If the type of material used in construction does not match any of the materials referenced in the tables associated with those paragraphs, cyclic curves shall be generated for the materials.

After application of such curves, the ratcheting assessment is re-applied as shown in step 72 and a determination made as to whether at least one of the ratcheting criteria is met in step 74. If at least one of the ratcheting criteria is not met, the design or geometry of the component must be modified as shown in step 55. If at least one of the ratcheting criteria is met, then the fatigue analysis shown as step 76 and as further described in FIG. 4 is performed.

With reference to FIG. 4, the fatigue analysis, which includes a fracture analysis, of the present invention is now described. The fatigue analysis of FIG. 4, in addition to the other steps described below, is based on fracture mechanics algorithms generally described in ASME Section VIII, Division 3, Article KD-4 and API 579-1/ASME FFS-1, and such fracture mechanics algorithms are hereby incorporated by reference into this application.

In step 78, the process is commenced by establishing the minimum detectable flaw size at fatigue sensitive points by NDE methodology conducted during the QA process. Such assumed flaws for the fatigue analysis shall be no smaller than the smallest flow that can be demonstrated to be detectable by the NDE methodology. The NDE methodology is either the one delineated in ASME Section VIII, Division 3, Article KE-3, or such other advanced methodologies as appropriate for the components as known in the art. Such NDE methodology shall be applied to ensure that the smallest flaw is detected in the component, and such NDE methodology descriptions are hereby incorporated by reference into this application.

Following step 78, fracture analysis, referred to as a Level II analysis (as per the API 579/ASME FFS-1 definition (and hereby incorporated by reference), is performed as indicated in step 80. Such fracture analysis is performed with respect to the equipment component to determine whether the equipment component satisfies certain fracture criteria. Such fracture criteria are based on minimum flaw size criteria and established toughness data. If the equipment component fails such analyses at hydrostatic test loads 82, design changes shall be made to the equipment component as indicated in step 83. If such design changes are minor, only the fracture/fatigue analysis of step 76 is performed. If such design changes are major, then the elastic-plastic finite element model of step 50 is re-performed and the entire process of step 50 through step 76 is repeated. Also, if the equipment component does not fail the fracture analysis in step 82, the equipment component is further analyzed for fatigue damage at fatigue sensitive locations in step 84. Such fatigue sensitive locations are those locations that have a total peak von Mises stress range at a node from the analysis conducted to determine the local strain limit damage (fine mesh model) greater than $\frac{2}{3}^{rd}$ of the specified minimum yield strength of the material considering the "worst case" preset load conditions sequence. The FEA mesh shall be fine enough to capture the effects of local stress concentrations. Alternatively, a stress intensification factor shall be applied.

The fatigue assessment of step 84 utilizes appropriate fatigue crack growth rates. The performance of the materials qualification process discussed above should have identified whether the downhole environment would have any impact on the fatigue crack growth rate. If there is any impact, then the air fatigue crack growth rates cannot be utilized as described in step 86. However, if there is no impact of the environment on the fatigue growth rate, then air fatigue crack growth rates are utilized. These rates may be generated in a laboratory or obtained from appropriate literature or ASME or API literature may be utilized. In such step, it is determined whether the equipment component satisfies fatigue criteria wherein such fatigue criteria are based on minimum flaw size criteria, established or inert environment toughness data and concurrent stress corrosion crack growth data.

The crack depth experienced by the equipment component is determined in step 88 for use in the design fatigue life assessment. It is determined in such step whether a pre-existing flaw in the equipment component identified in the analysis grows due to fatigue through any cladding overlay covering such equipment component to ensure that the flaw does not penetrate the cladding overlay.

The fatigue analysis shall be conducted in accordance with ASME Section VIII, Division 3, Article KD-4, with modifications as described below. Such description of such analysis is hereby incorporated by reference into this application. First, the contribution of each load to crack growth shall be considered. The preset load conditions shall be applied in the expected sequence, except that if the sequence is not known, they shall be applied in the sequence that causes the greatest total crack growth (shortest design fatigue life). The crack tip stress intensity calculations and reference stress calculations for steps 80 through 88 are generally contemplated and described in API 579-1/ASME FFS-1, 2007 Edition with errata and editorial changes through September, 2010. Such calculations are hereby incorporated by reference into this application. Further, the weight function method is preferred, but the third or fourth order curve fit methods in API 579-1/ASME FFS-1, 2007 Edition with errata and editorial changes through September, 2010 may be used if a single equation can be derived that is suitable for the stress distribution from the FEA. Such methods are hereby incorporated by reference into this application. If the equipment component includes clad or weld overlay construction, the maximum depth of the crack (i.e. the critical crack size) shall be the depth at which the crack reaches the base material. All cladding and weld overlay shall also meet the requirements of ASME Section VIII, Division 3, Article KF-3, and such requirements are hereby incorporated by reference into this application. Finally, the design fatigue life shall be determined using the factors in ASME Section VIII, Division 3, Article KD-4, (except that the factor of the number of cycles to ¼ of the critical crack depth does not apply to components with a wall thickness or crack growth path of less than 2 inches), or API 579-1/ASME FFS-1, and such factors are hereby incorporated by this reference into this application.

Components may be cladded with corrosion resistant alloy materials to ensure corrosion resistance in the HPHT environments. For such components, the fatigue criterion is the condition that during the anticipated life of the component the assumed pre-existing flaws not penetrate the cladding overlay due to fatigue. If such a growth is anticipated, the cladding overlay thickness must be increased to ensure that fatigue cycling does not compromise the corrosion resistance. Pre-existing flaws will be established using appropriate NDE (otherwise known as non-destructive evaluation) methodologies.

In the preferred embodiment, there are three different options for acceptance criteria for fatigue. One such criterion is that following anticipated fatigue cycles the crack size is lower than 25% of the critical crack size. A second criterion is that the number of fatigue cycles anticipated is less than 50% of that required to get to critical crack size. Finally, a third criterion is the safety factors from API 579-1/ASME FFS-1 that can be utilized to establish critical crack size limits following fatigue cycling. Such API 579 safety factors are hereby incorporated by this reference. If any one of these acceptance criteria is fulfilled, then the equipment component is confirmed for use in the HPHT environment in step 94. If the acceptance criteria are not fulfilled for fatigue, then a re-assessment of the load cycles applied to the equipment component shall be made to determine whether such loads are realistic given the anticipated HPHT environment for the equipment component. The crack growth rate, da/dN, shall be determined for the materials of construction in the environment the component will be exposed to unless it can be determined that the environment will not influence crack growth. This re-assessment is indicated as step 90. If the re-assessment does not confirm acceptance as determined in step 92, the equipment component shall require design changes as further shown in step 83. These design changes may either be minor and require re-performance of step 76 or major and require re-performance of step 50. If pursuant to such re-assessment, it is determined that the fatigue acceptance criteria described previously are met for typical environmental conditions, then the equipment component is confirmed for use in the HPHT environment in step 94. The performance of the confirmation step in step 94 concludes the design verification and validation process.

The materials qualification process and the design verification and validation process described above are implemented, in part, on a computer system as known in the art that includes a processor, memory, input/output devices, and software and the software includes instructions for execution of certain steps of the processes.

Although a preferred embodiment of the present invention has been described in the foregoing Detailed Description and has been illustrated in the accompanying Figures, it will be understood that the invention is not limited to the embodiment disclosed but is capable of numerous modifications without departing from the scope of the invention claimed. Also, although the methods disclosed herein have been described and shown with reference to particular steps performed in a particular order, it will be understood that these steps may be combined, sub-divided or re-ordered to form an equivalent method without departing from the teachings of the present invention. Accordingly, unless specifically indicated herein, the order and groupings of the steps are not a limitations of the present invention.

What is claimed is:

1. A method for design verification and validation of surface and sub-surface oil and gas equipment components comprising the steps of:
    (a) analyzing the components for global static strength and local plasticity with an elastic-plastic finite element model, the analysis using preset load conditions and the least favorable combination of dimensional tolerances for each component based on an initial mesh density and comprising the steps of:
        (i) confirming that the design of the component results in a stable model convergence using all preset load conditions;
        (ii) conducting a mesh refinement study on stressed portions of the components, where further refinement in mesh density will result in less than a pre-selected mesh refinement percentage change in plastic strain;
        (iii) confirming that stressed portions of the components identified by the model have strain limit damage that is less than a set strain limit damage amount;
    (b) conducting a ratcheting assessment by running an elastic-perfectly plastic analysis with the model on all equipment components that exhibit local plasticity at a maximum combination of preset load conditions to determine resistance to ratcheting by applying the maximum preset load conditions to such components to demonstrate at least one ratcheting criterion; and
    (c) examining all components to determine fatigue sensitive locations and subjecting components exhibiting fatigue sensitive locations to a fatigue analysis.

2. The method of claim 1 wherein the high pressure high temperature surface and sub-surface oil and gas equipment components tested are selected from the group of subsurface safety valves, wellhead trees, blowout preventers, or wireline pressure control equipment.

3. The method of claim 1 wherein the ratcheting criteria are selected from the group comprising a condition of no plastic action in the component, a condition where an elastic core exists at a primary load bearing boundary of the component, or a condition in which there is no permanent change in the dimensions of the component.

4. The method of claim 1 wherein the pre-selected mesh refinement percentage change is less than 5%.

5. The method of claim 1 wherein the pre-selected mesh refinement percentage change is less than 2%.

6. The method of claim 1 wherein the mesh refinement process refines an initial mesh density by a factor of 2.

7. The method of claim 1 wherein the set strain limit damage amount is 1.

8. The method of claim 1 wherein the ratcheting assessment includes the application of the preset load conditions to the component through at least 5 cycles.

9. The method of claim 1 wherein the elastic-plastic element finite element model is applied to the equipment components including all cladding overlay covering such equipment components.

10. The method of claim 1 wherein the preset load conditions include a set of load combinations based on the high temperature high pressure environment.

11. The method of claim 1 wherein the fatigue analysis further comprises a step of performing a fracture analysis on the equipment component to determine whether the equipment component satisfies certain fracture criteria wherein such fracture criteria are based on minimum flaw size criteria and established toughness data.

12. The method of claim 1 wherein the fatigue analysis further comprises the step of determining whether the equipment component satisfies fatigue criteria wherein such fatigue criteria are based on minimum flaw size criteria, established or inert environment toughness data and concurrent stress corrosion crack growth data.

13. The method of claim 12 wherein the fatigue analysis further determines whether a pre-existing flaw in the equipment component identified in the analysis grows through any cladding overlay covering such equipment component to ensure that the flaw does not penetrate the cladding overlay.

14. The method of claim 1 further comprising a materials qualification process to determine whether the materials used for the design of the equipment components are suitable for the high pressure high temperature environment.

15. The method of claim 14 wherein the materials qualification process experimentally establishes true stress-strain curve inputs for such materials.

16. The method of claim 1 further comprising, as a first and second step, the steps of:
(aa) providing at least one component;
(bb) obtaining data from the component to generate a computer readable representation of the component.

17. The method of claim 16, wherein the data obtained from the component is derived from a physical testing technique.

18. The method of claim 1 further comprising, as a first and second step, the steps of:
(aa) providing materials of a type used for construction of the components;
(bb) obtaining data from the materials using physical testing techniques to generate computer readable data inputs for use in the modeling of the components.

19. An apparatus designed for use in oil and gas wells in a high pressure high temperature environment, including for drilling, completion and production operations, the apparatus including components analyzed using a computer system including a processor, memory, input/output devices, and software, the software including instructions for execution of the computer system, having the characteristics comprising:
(a) when analyzed using the computer system for global static strength and local plasticity using an elastic-plastic finite element model with respect to certain preset load conditions and using the least favorable combination of dimensional tolerances for each component and based on an initial mesh density, the components:
(i) achieve a stable model convergence using all preset load conditions;
(ii) exhibit a mesh density where further refinement in mesh density of stressed portions of the components will result in less than a pre-selected mesh refinement percentage change in plastic strain;
(iii) achieve a strain limit damage for the stressed portions of the components identified by the model that is less than a set strain limit damage amount;
(b) when subjected to a ratcheting assessment by elastic-perfectly plastic analysis using the computer system, components that exhibit local plasticity at the maximum combination of preset load conditions are resistant to ratcheting using the preset load conditions by demonstrating at least one ratcheting criterion; and
(c) achieve acceptance criteria when the fatigue sensitive locations of the components are subjected to a fatigue analysis using the computer system.

20. The apparatus of claim 19 further comprising components that are analyzed that are not exposed to well produced fluids in an actual well environment.

21. The apparatus of claim 19 further comprising components that are analyzed that are not exposed to well kill fluids in an actual well environment.

22. The apparatus of claim 19 further comprising components that are analyzed that are not exposed to drilling and completion fluids in an actual well environment.

23. The apparatus of claim 19 wherein the components are selected from the group of subsurface safety valves, wellhead trees, blowout preventers, or wireline pressure control equipment.

24. The apparatus of claim 19 wherein the components are further subjected to a materials qualification process to determine whether the materials used for the design of the equipment components are suitable for the high pressure high temperature environment.

25. The apparatus of claim 24 wherein the materials qualification process experimentally establishes true stress-strain curve inputs for such materials.

26. The apparatus of claim 19 wherein the ratcheting criteria are selected from the group comprising a condition of no plastic action in the component, a condition where an elastic core exists at a primary load bearing boundary of the component, or a condition in which there is no permanent change in the dimensions of the component.

27. The apparatus of claim 19 wherein the pre-selected mesh refinement percentage change is less than 5%.

28. The apparatus of claim 19 wherein the pre-selected mesh refinement percentage change is less than 2%.

29. The apparatus of claim 19 wherein the mesh refinement process refines an initial mesh density by a factor of 2.

30. The apparatus of claim 19 wherein the set strain limit damage amount is 1.

31. The apparatus of claim 19 wherein the apparatus is constructed prior to the performance of the analysis by the computer system and data obtained from the apparatus using physical testing techniques is used to generate a computer readable representation of the apparatus for use in the analysis by the computer system.

32. The apparatus of claim 19 wherein materials of a type to be used to construct the components are tested using physical testing techniques and data obtained from the testing is used to generate computer readable data inputs for use in the analysis by the computer system.

33. A computer system for the design verification and validation of surface and sub-surface oil and gas equipment components including a processor, memory, input/output devices, and software, the software including instructions for execution of the computer system, the instructions comprising:
(a) analyzing the components for global static strength and local plasticity with an elastic-plastic finite element model, the analysis using preset load conditions and the least favorable combination of dimensional tolerances for each component based on an initial mesh density and comprising the steps of:
(i) confirming that the design of the component results in a stable model convergence using all preset load conditions;
(ii) conducting a mesh refinement study on stressed portions of the components, where further refinement in mesh density will result in less than a pre-selected mesh refinement percentage change in plastic strain;
(iii) confirming that stressed portions of the components identified by the model have strain limit damage that is less than a set strain limit damage amount;
(b) conducting a ratcheting assessment by running an elastic-perfectly plastic analysis with the model on all equipment components that exhibit local plasticity at a maximum combination of preset load conditions to determine resistance to ratcheting by applying the maximum preset load conditions to such components to demonstrate at least one ratcheting criterion; and
(c) examining all components to determine fatigue sensitive locations and subjecting components exhibiting fatigue sensitive locations to a fatigue analysis.

34. The computer system of claim 33 wherein the high pressure high temperature surface and sub-surface oil and gas equipment components tested are selected from the group of subsurface safety valves, wellhead trees, blowout preventers, or wireline pressure control equipment.

35. The computer system of claim 33 wherein the ratcheting criteria are selected from the group comprising a condition of no plastic action in the component, a condition where an elastic core exists at a the primary load bearing boundary of the component, or a condition in which there is no permanent change in the dimensions of the component.

36. The computer system of claim 33 wherein the preselected mesh refinement percentage change is less than 5%.

37. The computer system of claim 33 wherein the preselected mesh refinement percentage change is less than 2%.

38. The computer system of claim 33 wherein the mesh refinement process refines an initial mesh density by a factor of 2.

39. The computer system of claim 33 wherein the set strain limit damage amount is 1.

40. The computer system of claim 33 wherein the instructions further comprise performing a materials qualification process to determine whether the materials used for the design of the equipment components are suitable for the high pressure high temperature environment.

41. The computer system of claim 40 wherein the materials qualification process experimentally establishes true stress-strain curve inputs for such materials.

42. The computer system of claim 33 further comprising, as a first instruction, the instruction comprising generating a computer readable representation of the components obtained from data developed from the performance of physical testing techniques on the components.

43. The computer system of claim 33 further comprising, as a first instruction, the instruction comprising generating computer readable data inputs obtained from data developed from the performance of physical testing techniques on the materials of a type to be used to construct the components.

* * * * *